United States Patent
Fang et al.

(10) Patent No.: US 9,446,996 B2
(45) Date of Patent: Sep. 20, 2016

(54) REACTOR AND ALKYLATION PROCESS USING THE REACTOR

(71) Applicants: China Petroleum & Chemical Corporation, Beijing (CN); Fushun Research Institute of Petroleum And Petrochemicals, Sinopec, Fushun, Liaoning (CN)

(72) Inventors: Xiangchen Fang, Liaoning (CN); Deqiang Peng, Liaoning (CN); Huimin Qi, Liaoning (CN); Xin Li, Liaoning (CN); Yan Wang, Liaoning (CN); Jianbing Chen, Liaoning (CN); Luyao Wang, Liaoning (CN); Zhiyu Liu, Liaoning (CN); Xin Chen, Liaoning (CN); Shengzhong Zhang, Liaoning (CN)

(73) Assignees: CHINA PETROLEUM & CHEMICAL CORPORATION, Beijing (CN); FUSHUN RESEARCH INSTITUTE OF PETROLEUM AND PETROCHEMICALS, SINOPEC, Fushun, Liaoning (CN)

(*) Notice: Subject to any disclaimer, the term of this patent is extended or adjusted under 35 U.S.C. 154(b) by 254 days.

(21) Appl. No.: 14/067,386

(22) Filed: Oct. 30, 2013

(65) Prior Publication Data
US 2014/0128654 A1 May 8, 2014

(30) Foreign Application Priority Data

Nov. 3, 2012 (CN) .......................... 2012 1 0432675
Nov. 3, 2012 (CN) .......................... 2012 1 0432683

(51) Int. Cl.
*B01J 8/10* (2006.01)
*B01J 19/28* (2006.01)
(Continued)

(52) U.S. Cl.
CPC ................. *C07C 2/62* (2013.01); *B01J 4/002* (2013.01); *B01J 14/00* (2013.01); *B01J 19/006* (2013.01);
(Continued)

(58) Field of Classification Search
CPC ............. C07C 2/62; B01J 4/00; B01J 10/02; B01J 19/28; B01J 8/10
USPC ......................................................... 422/209
See application file for complete search history.

(56) References Cited

U.S. PATENT DOCUMENTS 2,438,852 A * 3/1948 Goldsby .................. C07C 2/58
366/325.2
2,463,262 A * 3/1949 Goldsby .................. C07C 2/58
159/6.1
(Continued)

FOREIGN PATENT DOCUMENTS

CN 1184797 A 6/1998
CN 1743064 A 3/2006
(Continued)

OTHER PUBLICATIONS

English translation of CN-1743064 A—Jan. 6, 2016.*
(Continued)

*Primary Examiner* — Huy-Tram Nguyen
(74) *Attorney, Agent, or Firm* — Novick, Kim & Lee, PLLC; Allen Xue (57) ABSTRACT

The present disclosure provides a reactor for at least two liquid materials, comprising an enclosed reactor housing; a feeding tube having liquid material inlets for receiving corresponding liquid materials respectively; a distribution tube communicating with the feeding tube and extending into the reactor housing, the distribution tube being provided with a plurality of distribution holes in the region thereof extending into the reactor housing; a rotating bed in form of a hollow cylinder, which is disposed in the reactor housing via a fixing mechanism, thus dividing inner cavity of the reactor housing into a central area and an outer area, the rotating bed being capable of rotating driven by a driving mechanism; and a material outlet provided in a lower portion of the reactor housing for outputting product after reaction. The distribution tube extends into the central area spaced from inner surface of the rotating bed, so that materials can enter into the outer area from the central area through the rotating bed and can be output via the material outlet.

28 Claims, 2 Drawing Sheets (51) Int. Cl.
*B01J 10/02* (2006.01)
*C07C 2/62* (2006.01)
*B01J 14/00* (2006.01)
*B01J 19/00* (2006.01)
*B01J 19/18* (2006.01)
*B01J 4/00* (2006.01)

(52) U.S. Cl.
CPC ............ *B01J 19/1806* (2013.01); *B01J 19/28* (2013.01); *B01J 2219/00094* (2013.01); *B01J 2219/00189* (2013.01); *B01J 2219/00768* (2013.01); *C07C 2527/054* (2013.01)

(56) References Cited

U.S. PATENT DOCUMENTS

| | | | |
|---|---|---|---|
| 3,431,085 A * | 3/1969 | Cimerol | B01J 19/18 210/179 |
| 4,218,575 A | 8/1980 | Webb, Jr. | |
| 4,236,036 A | 11/1980 | Dixon et al. | |
| 4,479,720 A | 10/1984 | Mochida et al. | |
| 5,264,645 A | 11/1993 | Hugues et al. | |
| 5,785,933 A * | 7/1998 | Cunningham | B01J 4/004 422/215 |
| 7,569,196 B2 * | 8/2009 | Zanthoff | B01F 7/00641 210/225 |
| 7,652,187 B2 | 1/2010 | Bakshi | |
| 7,947,232 B2 * | 5/2011 | Strauss | B01J 4/001 165/145 |
| 2003/0043689 A1 * | 3/2003 | Jang | B01F 5/0057 366/165.2 |
| 2005/0167641 A1 * | 8/2005 | Chen | B82Y 30/00 252/604 |
| 2006/0147357 A1 | 7/2006 | Leveson | |
| 2008/0171889 A1 | 7/2008 | Chen et al. | |
| 2010/0185022 A1 | 7/2010 | Raston et al. | |

FOREIGN PATENT DOCUMENTS

| | | |
|---|---|---|
| CN | 1765487 | 5/2006 |
| CN | 1907924 A | 2/2007 |
| CN | 102218291 A | 10/2011 |
| CN | 102276472 A | 12/2011 |
| CN | 202122946 U | 1/2012 |
| EP | 0003907 A1 | 9/1979 |
| WO | 00/48732 A1 | 8/2000 |
| WO | 2012/034164 A2 | 3/2012 |

OTHER PUBLICATIONS

Ke, Ming El Al "Study on Alkylation of Isobutane with Petenes Using Sulfuric Acid as a Catalyst" Petrochemical Industry Technology, 2002, Issue 9, vol. 3, pp. 150-153.

Zhigang Liu et al "Review of Alkylation's Process of Isobutane with Butene" Natural Gas and Oil, vol. 20 No. 2, Jun. 2002.

* cited by examiner

REACTOR AND ALKYLATION PROCESS USING THE REACTOR

TECHNICAL FIELD

The present disclosure relates to a reactor, especially to a reactor used for alkylation reaction. The present disclosure further relates to a process of alkylation reaction using the reactor, specifically to catalytic alkylation reaction using isobutane and C3~C5 olefins.

TECHNICAL BACKGROUND

Vehicle exhaust emissions have become a major source of air pollution with the rapid development of transportation. The improvement of gasoline quality is the most important way to reduce vehicle exhaust emissions. It is known that alkylate oils obtained from alkylation reaction between isobutane and C3~C5 olefins are sulfur-free, of high octane and small differences between research octane number and motor octane number, so that they can be used as an important blending component of high quality clean gasoline.

As a conventional technology in the field of oil refining, alkylation reaction mainly includes sulfuric acid alkylation technology and hydrofluoric acid alkylation technology, wherein isoparaffins are obtained through reaction between isobutane and olefins in the presence of a catalyst (sulfuric acid or hydrofluoric acid). The sulfuric acid alkylation method and the hydrofluoric acid alkylation method are of different technological characteristics and very close to each other in infrastructure investment, production costs, product yield, product quality, etc. Therefore, these two methods coexist in a very long period and are both widely adopted. Generally, the hydrofluoric acid alkylation apparatuses excel in apparatus number and alkylate oil yield at present. However, as environment regulations are becoming increasingly strict and due to toxic properties of hydrofluoric acid, new apparatuses tend to adopt sulfuric acid alkylation processes in recent years.

In the sulfuric acid alkylation technology, reaction is carried out in a relatively low temperature and therefore the reaction apparatuses need to possess a cooling function. In the hydrofluoric acid alkylation technology, the reaction temperatures are relatively high, so that water-cooling can generally meet the requirements. As a result, the two reactor systems are quite different from each other. Conventional sulfuric acid alkylation reactors include various types of structures, among which two are mainly used currently. They are the stepped sulfuric acid alkylation unit and the Stratco reactor (i.e., an indirect cooling reactor provided with an internal warm-taking bundle).

The reactor of the stepped sulfuric acid alkylation unit generally comprises a plurality of reaction sections, wherein the sections are separated from one another with overflow baffles and each reaction section is provided with a stirrer. The reaction products and sulfuric acid finally enter into a precipitation section to be separated and the separated sulfuric acid is introduced to a reaction section for reuse via a circulation pump, wherein the automatic evaporative cooling of the reactant isobutane is adopted. This reaction system is advantageous in that each reaction section has a high paraffin-olefin ratio and small power consumption, with no additional coolant being required. However, since the paraffins and olefins are not pre-mixed, the quality of alkylate oils is reduced and the acid consumption is increased. In addition, reactions in different sections interact with one another, so that when an abnormal operation occurs in one reaction section, the entire reactor would be affected.

One specific structure for the indirect cooling reactor provided with an internal warm-taking bundle adopts a horizontal eccentric reactor. The reactor comprises a horizontal pressure vessel as a housing, and is provided with a powerful stirrer, a circulating sleeve and a thermal-taking bundle inside the reactor. Hydrocarbon feedstocks which are fed into the reactor through one upper and one lower material inlets are mixed before a stirring impeller and then sprayed toward the impeller into the reactor. The high-speed rotating impeller is arranged at a reduced diameter portion of the reactor, so that streams inside the reactor produce a plurality of fluid flowing cavities due to impeller suction, bundle resistance, linear speed differences, etc. Therefore, sulfuric acid and hydrocarbons can be better dispersed and mixed. An emulsion of acid and hydrocarbons returns to an interior portion of the sleeve at a head portion of the reactor and flows back to the stirring impeller so as to form a high-speed circulating stream. The reactor comprises circulating materials therein. Because part of the materials react for a relatively long time, side reactions are increased and acid consumption is relatively large, which is disadvantageous for improving the octane number of the product.

U.S. Pat. No. 7,652,187 discloses a sulfuric acid alkylation process between C3~C5 olefins and isobutane, wherein instead of the conventional mechanical stirring method, an injector is adopted to mix the reactants for reaction. However, in the sulfuric acid alkylation process, because there is a great difference between sulfuric acid and hydrocarbon materials in density, the jet mixing effect is still to be improved. U.S. Pat. No. 5,785,933 discloses a reactor system of sulfuric acid catalytic alkylation, wherein a baffle and a plurality of tangentially arranged injection pipe inlets are provided inside the reactor, so that the reactants are stirred and mixed in the reactor and mechanical moving components are unnecessary. In this technology, the static mixer principle is adopted to design a sulfuric acid alkylation reactor, but the mixing effect thereof is still to be improved.

Chinese Pat. No. 1907924A discloses an ionic liquid catalytic reaction process and a reaction apparatus, wherein hydrocarbon materials and ionic liquid catalysts react in a rotating bed reactor which is arranged in an upper portion of the reactor. A lower portion of the reactor is provided with a fluid reservoir and a central portion of the reactor is provided with a stirring apparatus. The fluid reservoir is connected to a fluid material circulating pump to define the rotating bed circulating reactor. However, the reactor is not applicable in the sulfuric acid alkylation process, because it adopts circulating material heat removal, which is not suitable for sulfuric acid alkylation releasing a great amount of heat. Furthermore, the fluid reservoir in the lower portion of the reactor and reaction material circulating operations would increase side reactions.

SUMMARY OF THE INVENTION

To solve the above problems, the present disclosure aims to provide a reactor for at least two liquid materials. In the reactor, all the liquid materials can be fully mixed and then react with one another. Particularly, the present disclosure aims to provide an alkylation reactor and an alkylation process using the alkylation reactor, wherein the contacting efficiency of catalysts and hydrocarbon reactants can be improved, the acid consumption of sulfuric acid catalysts and the reaction temperatures can be reduced and the product quality can be improved.

According to a first aspect of the present disclosure, a reactor for at least two liquid materials is provided, comprising: an enclosed reactor housing; a feeding tube having liquid material inlets for receiving corresponding liquid materials respectively; a distribution tube communicating with the feeding tube and extending into the reactor housing, the distribution tube being provided with a plurality of distribution holes in the region thereof extending into the reactor housing; a rotating bed in form of a hollow cylinder, which is arranged in the reactor housing via a fixing mechanism, thus dividing inner cavity of the reactor housing into a central area and an outer area, the rotating bed being capable of rotating driven by a driving mechanism; and a material outlet disposed under the reactor housing for outputting product after reaction. The distribution tube extends into the central area spaced from inner surface of the rotating bed, so that materials can enter into the outer area from the central area through the rotating bed and can be output via the material outlet.

According to the present disclosure, the reactants must enter into the outer area from the central area radially through the rotating bed rotating at a high speed, wherein under the supergravity generated by the rotation of the rotating bed, all the liquid reactants are dispersed. The reactants fiercely impact on inner walls of bed layers of the rotating bed rotating at a high-speed, achieving an enhanced mixing. Meanwhile, when flowing through the bed layers of the rotating bed, the reactants are continuously cut by each bed layer, wherein a dispersion-aggregation process is repeatedly achieved, and thus the mixing effect is significantly enhanced.

Since the reactor according to the present disclosure uses a rotating bed instead of a mechanical stirring apparatus, lower reaction temperature can be adopted, which is especially suitable for sulfuric acid alkylation reaction. There are various advantages for sulfuric acid alkylation reaction to be carried out in low reaction temperature. For example, the octane number of the product can be improved; side reactions can be suppressed; the acid consumption can be lowered; so on and so forth. In the sulfuric acid alkylation technology using a conventional reactor, the reaction temperature is usually in a range from 4 to 10° C. because a reactor mainly adopts a mechanical stirring method in the prior art, where a low reaction temperature would significantly reduce the dispersion of the reactants (concentrated sulfuric acid has a large viscosity at low temperature). When the viscosity of concentrated sulfuric acid is greatly increased, concentrated sulfuric acid and hydrocarbon materials cannot form a sufficient dispersion system, so that when the reaction temperature is lower than 5° C., the reaction would be less effective. However, when the reactor according to the present disclosure is used to carry out sulfuric acid alkylation reaction, thanks to the supergravity generated in the rotation of the rotating bed, reactants of high viscosity can still be sufficiently dispersed, so that concentrated sulfuric acid and hydrocarbon materials can be fully dispersed and contact with one another, thus leading to ideal reaction effects. Tests have shown that when the method according to the present disclosure is implemented at −15° C., excellent reaction effects can still be achieved.

In addition, when the reactor according to the present disclosure is used, the scale of the reaction apparatus can be significantly reduced. In a sulfuric acid alkylation reaction, the reaction rate is mainly controlled by mass transfer steps because the solubility of isobutane in the concentrated sulfuric acid is relatively low and the mass transfer resistance is relatively large due to the two-phase reaction. When the reaction apparatus in the prior art is used, the reaction rate is relatively slow due to insufficient two-phase dispersion effect, so that a comparatively large reaction apparatus is required for the same reaction. In contrast, with the reactor of the present disclosure, the mass transfer steps can be significantly enhanced so that the reaction rate is increased, the required reaction time is shortened, the reaction apparatus scale is greatly reduced and thus the apparatus and operation costs are decreased.

In one embodiment, the distribution holes in the distribution tube are all arranged under an upper surface of the rotating bed, so that all the reactants from the distribution pipe are ensured to enter into the central area in the housing completely and thus they can pass through the rotating bed and be evenly mixed.

In one embodiment, the rotating bed is provided with a sealing mechanism. Specifically, the upper surface of the rotating bed is fixedly provided with a first annular plate, which rotatably and sealably connects to a second annular plate fixedly mounted on an inner wall of the reactor housing. The sealing mechanism formed by the first annular plate and the second annular plate can on the one hand ensure that any reactants in an upper portion of the rotating bed only enter into the central area instead of entering the outer area and on the other hand enhance the support to the rotating bed.

Preferably, a first flange is provided at a circumferential outer edge of the first annular plate and a second flange is provided at a circumferential inner edge of the second annular plate. The first and second flanges are sealably connected to each other in a relatively rotatable manner via a sealing member, so that rotatable connection in a sealable manner can be simply and effectively achieved.

The rotating bed comprises a corrosion-resistant frame and bed layers, which for example can be composed of a corrosion-resistant wire mesh or filler.

According to a preferred embodiment, a stationary bed fixedly connects to the reactor in the outer area, and is spaced from an outer side of the rotating bed, so that the materials from the rotating bed rotating at a high speed would impact on the stationary bed. After that, part of the materials pass through the stationary bed and part of them flow downstream along the stationary bed, so that an additional impact of the liquid phase is achieved, enhancing the mixing effect, which is beneficial for further adequate reaction. Therefore, with a stationary bed, the kinetic energy of the materials can be fully used and the same reaction effect can be achieved with relatively small power consumption. At the same time, the stationary bed can also facilitate the collection of vaporous liquid materials.

The stationary bed can extend around the rotating bed along a circumferential direction in a range from 180 to 360 degrees. Preferably, the stationary bed is completely circumferentially arranged around the rotating bed. The stationary bed can be fixed to the reactor housing at a lower or upper portion thereof, or fixed along a radial direction. For example, an upper end of the stationary bed can be fixedly arranged below the second annular plate. Alternately, the stationary bed is fixed in the inner wall of the reactor housing via a radial connecting member. Moreover, the stationary bed and the rotating bed can be of the same height and have the same axis. Nevertheless, the stationary bed can be arranged longer than the rotating bed, so that all the materials from the rotating bed can contact with the stationary bed. In one specific embodiment, an upper end of a chamber formed between the rotating bed and the stationary bed is closed by the second annular plate and a lower end thereof is open. The stationary bed can be 0.2 to 1.5 times, preferably 0.5 to 0.8 times as thick as the rotating bed.

According to one preferred embodiment, a circulating cooling medium inlet and a circulating cooling medium outlet, which are respectively arranged at two sides with respect to the upper surface of the rotating bed, are further provided to the reactor housing. The circulating cooling medium can be for example circulating cooling gas. Specifically, one of the circulating cooling medium inlet and the circulating cooling medium outlet is provided above the upper surface of the rotating bed is provided (i.e., above the sealing mechanism), and the other of them is provided below a lower surface of the rotating bed. When the circulating cooling medium inlet is provided above the sealing mechanism and the circulating cooling medium outlet is provided below the sealing mechanism, the circulating cooling medium flows in the same direction as the materials. Under this condition, the circulation of the circulating cooling medium can be achieved under a pumping action generated from the liquid phase materials to the vapor phase materials in the operation of the rotating bed. Therefore, no power transmission apparatus for the circulating cooling medium is necessary, so that a simple structure can achieved.

A medium refrigeration system preferably arranged outside the reactor is provided between the circulating cooling medium inlet and the circulating cooling medium outlet, so that the circulating cooling medium circulates between the refrigeration system and the rotating bed, which can facilitate a suitable temperature environment for the reaction.

Thus, according to the present disclosure, circulating cooling gas is adopted as the cooling medium, wherein vapor is continuous phase and liquid phase is dispersed phase. The reactants are dispersed in the circulating cooling medium in the form of tiny liquid droplets, which is completely different from the conventional indirect heat exchange and removal. Under the supergravity of the rotating bed, a micron-scale dispersion of the reactants can be achieved. The liquid phase materials are dispersed in the vapor phase cooling medium in the form of tiny particles, so that the heat exchange area is far larger than that of the indirect bundle heat exchange reactor. As a result, a more homogeneous reaction temperature can be achieved. Moreover, no hot spots are generated and the reaction temperature is homogeneous in a micron scale. In contrast, conventional reactors can only achieve a macroscopic homogeneous temperature, wherein regional hot spots cannot be excluded, which are sources of a series of adverse effects (such as decline in product quality and increase in acid consumption, etc.).

According to one preferred embodiment, at a top portion of the feeding tube a collision chamber is provided for premixing the liquid materials, wherein the liquid material inlets communicate with and enter into the collision chamber. Preferably, an injection pipe is provided at each of the liquid material inlets, the injection pipes being opposite to each other. The adoption of a jet mixer for premixing the liquid materials (concentrated sulfuric acid and hydrocarbon materials) can facilitate the impact between the two liquid phases and enhance the mixing effect.

According to one preferred embodiment, the fixing mechanism comprises a rotating shaft connecting to the driving mechanism and a support connecting to the rotating shaft, wherein the rotating bed is mounted on the support. In one specific embodiment, the driving mechanism comprises an electric motor provided outside the reactor housing.

The reactor according to the present disclosure is especially suitable for sulfuric acid alkylation reaction, wherein concentrated sulfuric acid and mixed hydrocarbons are supplied into the reactor for reaction.

According to a second aspect of the present disclosure, an alkylation reaction process is provided, wherein isobutane, mixed hydrocarbons of C3 to C5 olefins and a sulfuric acid catalyst are introduced into the above reactor for alkylation reaction.

In the process according to the present disclosure, the molar ratio of isobutane to C3 to C5 olefins can be in a range from 1:1 to 300:1, preferably from 3:1 to 50:1. The sulfuric acid catalyst can be concentrated sulfuric acid, wherein the volume ratio of the concentrated sulfuric acid to the mixed hydrocarbons is in a range from 0.1:1 to 5:1, preferably from 0.5:1 to 1.5:1 and the mass concentration of the concentrated sulfuric acid is in a range from 90% to 97%, preferably from 93% to 96%. The sulfuric acid after reaction can be separated and recycled. After the concentration of the concentrated sulfuric acid is decreased, fresh concentrated sulfuric acid can be supplemented to maintain a suitable concentration. The concentration of sulfuric acid is associated with the freezing point thereof, so that the concentration of the sulfuric acid in the reaction system shall match with the reaction temperature, i.e., the reaction temperature shall be higher than the freezing point of the concentrated sulfuric acid used in the reaction system.

In the process according to the present disclosure, the reaction temperature can be in a range from −20 to 15° C., preferably from −10 to 10° C. and more preferably from −5 to 5° C., and the reaction pressure can be maintained at a level when the mixed hydrocarbons are in a liquid phase, preferably in a range from 0.2 to 1.5 MPa and more preferably from 0.3 to 0.8 MPa.

In the process according to the present disclosure, the rotation speed of the rotating bed is in a range from 50 to 5,000 rpm, preferably in a range from 150 to 2,000 rpm. The residence time of the materials in the reactor ranges from 2 to 600 s, preferably from 10 to 100 s.

In the process according to the present disclosure, the reaction temperature is controlled with a circulating cooling medium, which can be nitrogen, hydrogen, inert gases, carbon monoxide, carbon dioxide, methane, ethane or propane, preferably nitrogen or methane. The refrigeration system of the circulating cooling system can be any refrigeration system in the prior art.

In one specific embodiment, liquid propane can be adopted as the cooling medium, when propane is introduced in the rotating bed reactor in the liquid phase and discharged therefrom in the vapor phase. Since liquid propane possesses large latent heat, its heat absorption capacity is so great that a good cooling effect can be achieved.

In the process according to the present disclosure, the materials after the reaction are precipitated and then subsequently separated, wherein sulfuric acid, alkylate oils generated in the reaction and unreacted materials are separated. Unreacted materials such as isobutane and olefins can be recycled.

BRIEF DESCRIPTION OF DRAWINGS

The present disclosure will be described in detail with reference to specific examples and drawings. It should be noted that the drawings are provided for better understanding of the present disclosure rather than to limit the present disclosure in any way. In the drawings, FIG. 1 schematically shows a reactor according to a first embodiment of the present disclosure.

DETAILED DESCRIPTION OF EMBODIMENTS

Figure 1:
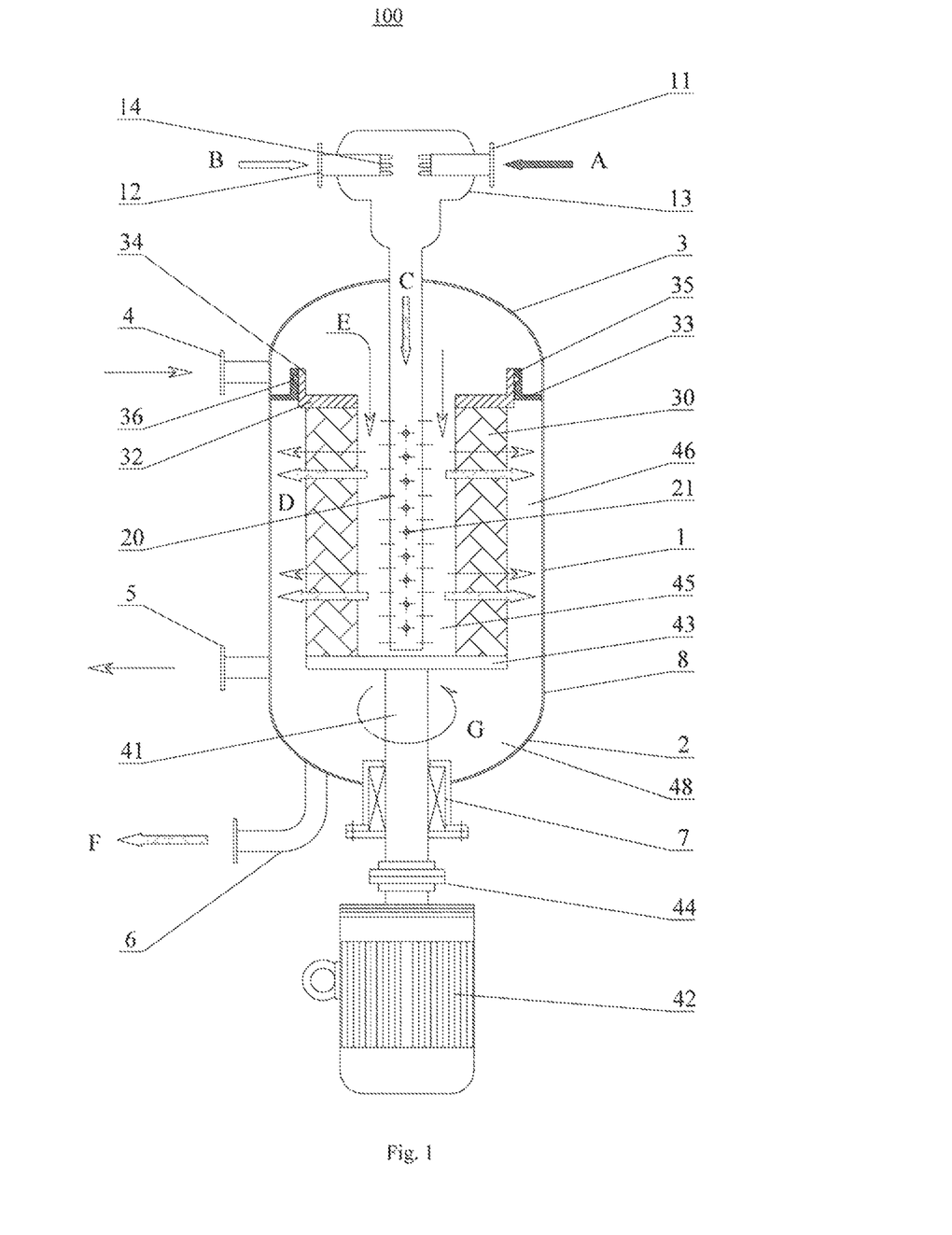

FIG. 1 schematically shows a reactor 100 according to a first example of the present disclosure. As shown in FIG. 1, the reactor 100 comprises a reactor housing 1, which comprises a straight pipe section 8, an upper head 3 and a lower head 2, so that a closed structure is defined. The reactor 100 further comprises a feeding tube 10 arranged outside the reactor housing 1, preferably arranged in an upper portion of the reactor housing 1. The feeding tube 10 has corresponding inlets for receiving various liquid materials respectively. For example, when the reactor 100 is used for alkylation reaction with sulfuric acid as the catalyst, the feeding tube 10 can comprise a first inlet 11 for receiving sulfuric acid and a second inlet 12 for receiving liquid hydrocarbons (such as isobutane and C3~C5 olefins). The specific structure of the feeding tube 10 will be described in detail in the following. A lower portion of the reactor housing 1 is provided with a material outlet 6. As shown in FIG. 1, sulfuric acid and liquid hydrocarbons enter into the feeding tube 10 along the directions as shown by Arrows A and B respectively, while reaction products leave the reactor housing 1 along the direction as shown by Arrow F.

The reactor 100 further comprises a distribution pipe 20, which communicates with the feeding tube 10 and extends inside the reactor housing 1 sealably through the upper head 3 of the reactor housing 1. A plurality of distribution holes 21 are provided on the region of the distribution pipe 20 which extends in a cavity 48 in the reactor housing 1. In the embodiment as shown in FIG. 1, these distribution holes 21 are arranged at a distance with one another along a longitudinal direction of the distribution pipe 20. In this manner, the reaction materials that have entered into the feeding tube 10 via the first inlet 11 and the second inlet 12 (such as sulfuric acid and liquid hydrocarbons) would enter into the distribution pipe 20 along the direction as shown by Arrow C and into the reactor housing 1 via the distribution holes 21.

According to the present disclosure, the reactor 100 can further comprise a rotating bed 30 provided in the reactor housing 1. The rotating bed 30 preferably comprises a corrosion-resistant frame and bed layers, each of which is preferably composed of a corrosion-resistant wire mesh or filler. As shown in FIG. 1, the rotating bed 30 can for example be in form of a hollow cylinder, which is arranged in the reactor housing 1 via a fixing mechanism 40. In the embodiment as indicated in FIG. 1, the fixing mechanism 40 comprises a support 43 for fixedly arranging the rotating bed 30 and a rotating shaft 41 connected to the support 43. The rotating shaft 41 extends outside the reactor housing 1 sealably through the lower head 2 of the reactor housing 1 and connects to a driving mechanism such as an electric motor 42 via a coupling 44. It can be easily understood that a sealing mechanism 7 can be used to seal the rotating shaft 41 and the reactor housing 1. Thus, when the electric motor 42 runs, the rotating bed 30 is driven to rotate via the rotating shaft 41, for example along the direction as indicated by Arrow G.

The rotating bed 30 in form of a hollow cylinder divides the inner cavity of the reactor housing into a central area 45 and an outer area 46. The distribution pipe 20 extends into the central area 45 at an interval from the rotating bed 30. Preferably, the distribution holes 21 arranged on the distribution pipe 20 are all provided at positions lower than an upper surface of the rotating bed 30, so that all the reaction materials leaving the distribution pipe 20 via the distribution holes 21 can be ensured to enter into the central area 45 completely.

A sealing mechanism 31 which comprises a first annular plate 32 fixed to an upper surface of the rotating bed 30 and a second annular plate 33 fixedly mounted on an inner wall of the reactor housing 1, is provided between an upper portion of the rotating bed 30 and the reactor housing 1. The first annular plate 32 and the second annular plate 33 together form a rotatable sealing connection. In the embodiment as shown in FIG. 1, a first flange 34 is provided at a circumferential outer edge of the first annular plate 32, while a second flange 35 is provided at a circumferential inner edge of the second annular plate 33. The first flange 34 and the second flange 35 are sealably connected to each other in a relatively rotatable manner via a sealing member 36 (and necessary bearings). The first annular plate 32 and the second annular plate 33 at an upper side and the support 43 at a lower side on the one hand reinforce the support to the rotating bed 30, and on the other hand enable any material above the rotating bed 30 to only enter into the central area 45 instead of directly entering into the outer area 46.

In the reactor 100 according to the present disclosure, reaction materials (such as sulfuric acid and liquid hydrocarbons) first enter into the feeding tube 10 via the first inlet 11 and the second inlet 12, leave the distribution pipe 20 through the distribution holes 21 and enter into the central area 45. Afterwards, the reaction materials radially pass through the rotating bed 30 along the direction indicated by fat-Arrow D as shown in FIG. 1 before entering into the outer area 46 of the cavity of the reactor housing 1. In the end, after the reaction materials are collected at the lower head 2 of the reactor housing under the gravity thereof, they flow out of the reactor 100 via the material outlet 6. Thus, the reaction is completed.

According to the present disclosure, the reaction materials must radially pass through the rotating bed 30 rotating at a high speed driven by the electric motor 42. Under the supergravity generated by the rotation of the rotating bed 30, the liquid reaction materials are dispersed and fiercely impact on inner walls of the bed layers of the rotating bed rotating at a high speed to realize fortified blending. Meanwhile, when flowing through the bed layers of the rotating bed 30, the reaction materials are continuously cut by each bed layer, wherein a dispersion-aggregation process is repeatedly achieved, and thus the mixing effect is significantly enhanced.

According to the present disclosure, the reactor housing 1 further comprises a circulating cooling medium inlet 4 and a circulating cooling medium outlet 5, where between a circulating gas refrigeration system is provided. Thereby, the circulating cooling medium circulates between the refrigeration system and the rotating bed, facilitating a suitable temperature environment for the reaction processes. The circulating gas refrigeration system can be provided either at an outer portion or an inner portion of the reactor housing 1. In a preferred embodiment, the circulating gas refrigeration system can be provided at the outer portion of the reactor housing 1.

In one design, with reference to the sealing mechanism 31, the circulating cooling medium inlet 4 is located above the sealing mechanism 31, while the circulating cooling medium outlet 5 is located below the sealing mechanism 31.

Under this condition, the circulating cooling medium flows in a direction as indicated by thin-Arrow E and passes through the rotating bed 30 in the same direction as the reaction materials. Thanks to a pumping action generated by the rotating bed 30 rotating at a high speed to the gas, a power apparatus for conveying the circulating cooling medium is not necessary to be provided. Alternately, a small power apparatus for conveying the circulating cooling medium can be provided. In another design, with reference do the sealing mechanism 31, the circulating cooling medium inlet 4 is located below the sealing mechanism 31, while the circulating cooling medium outlet 5 is located above the sealing mechanism 31. Under this condition, the circulating cooling medium would pass through the rotating bed 30 in a direction opposite to the flowing direction of the reaction materials and therefore, a power apparatus for conveying the circulating cooling medium is necessary.

Thus, according to the present disclosure, circulating cooling gas is adopted as the cooling medium, wherein the vapor is continuous phase and the liquid is dispersed phase. The reactants are dispersed in the circulating cooling medium in the form of tiny liquid droplets, which is completely different from conventional indirect heat exchange and removal. Under the supergravity of the rotating bed 30, a micron-scale dispersion of the reactants can be achieved.

The liquid phase materials are dispersed in the vapor phase cooling medium in the form of tiny particles, so that the heat exchange area is far larger than that of the indirect bundle heat exchange reactor. As a result, a more homogeneous reaction temperature can be achieved. Moreover, no hot spots are generated and the reaction temperature is homogeneous in a micron scale. In contrast, conventional reactors can only achieve macroscopic homogeneous temperature, wherein regional hot spots cannot be excluded, which are sources of a series of adverse effects (such as decline in product quality and increase in acid consumption, etc.).

Additionally, in the present disclosure, the pumping action of liquid-phase materials to vapor-phase materials can be used to drive the vapor-phase materials to flow from the central area to the outer area, so as to achieve sufficient and effective cooling to highly dispersed liquid materials by the vapor-phase materials as a continuous cooling medium and further achieve high uniformity of the temperature field.

According to a preferred embodiment, the reactor 100 according to the present disclosure further comprises a collision chamber 13 arranged at a top portion of the feeding tube 10. The first inlet 11 and the second inlet 12 for receiving liquid materials both communicate with and enter into the collision chamber 13 so as to facilitate the premixing of various materials therein. Preferably, the inlets 11 and 12 are both provided with an injection pipe with the injection pipes configured to be diametrically opposite to each other. Thereby, excellent clashing dispersion effect can be ensured and thus excellent premixing of various materials can be achieved. In one specific embodiment, the injection pipe comprises a plurality of nozzles, the sum area of which is ⅓ to ⅘ as large as that of a feeding connection tube.

Figure 2:
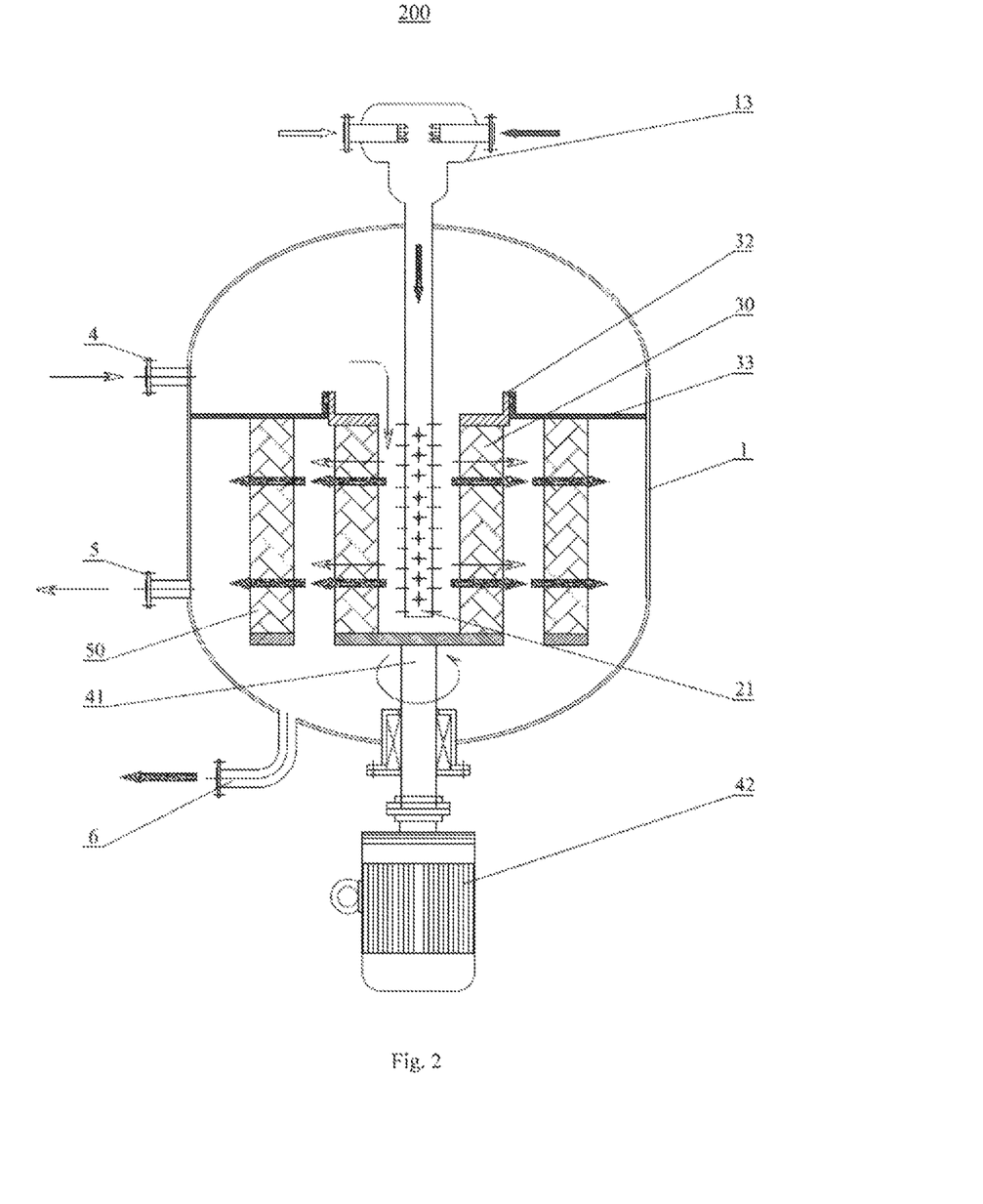
FIG. 2 schematically shows a reactor according to a second embodiment of the present disclosure.

FIG. 2 schematically shows a reactor 200 of a second embodiment according to the present disclosure. For the sake of simplicity, only the differences of the reactor 200 from the reactor 100 will be discussed in the following. Reference can be made to the reactor 100 as mentioned above for the similarities.

As indicated in FIG. 2, the reactor 200 further comprises a stationary bed 50 provided in the outer area 46. The stationary bed 50 is preferably coaxially arranged outside the rotating bed 30 and is spaced from an outer side of the rotating bed 30. A bed layer of the stationary bed 50 can for example be composed of a corrosion-resistant screen, wire mesh or filler. The stationary bed 50 is circumferentially arranged around the rotating bed 30 for at least a half circle, preferably one circle, i.e., the stationary bed is circumferentially arranged around the rotating bed 30 completely.

The stationary bed 50 can be fixed to the reactor housing 1 at a lower portion or upper portion thereof, or fixed along a radial direction. FIG. 2 indicates that the stationary bed 50 is fixed at a lower portion of the sealing mechanism 31, specifically fixed at a lower portion of the second annular plate 33, so that an upper end of a chamber defined between the rotating bed 30 and the stationary bed 50 is closed by the second annular plate 33 and a lower end of the chamber is open. It can be easily understood that one skilled in the art can fix the stationary bed 50 to the reactor housing 1 via a lower connecting member or a radial connecting member as required.

With the stationary bed 50, the materials with a high speed from the rotating bed 30 would impact on the stationary bed 50, so that a secondary impact of the liquid phase is achieved, thus reinforcing the mixing effect, which can facilitate further sufficient reaction. Therefore, with a stationary bed 50, the kinetic energy of the materials can be fully used and the same reaction effect can be achieved with relatively small power consumption. At the same time, the stationary bed 50 can also facilitate the collection of vaporous liquid materials.

The stationary bed 50 and the rotating bed 30 can be of the same height. Nevertheless, the stationary bed 50 can be longer than the rotating bed 30, so that all the materials from the rotating bed 30 can impact on the stationary bed 50 completely. The distance between the stationary bed 50 and the rotating bed 30 can for example be 10 mm to 700 mm, preferably 50 mm to 200 mm. The stationary bed 50 can be 0.2 to 1.5 times, preferably 0.5 to 0.8 times as thick as the rotating bed.

In the following the reaction effects of the present disclosure will be described with reference to examples and comparative examples.

Examples 1 to 3

The reactor 100 as indicated in FIG. 1 is adopted. The rotating bed layers comprise stainless steel mesh fillers and the bed voidage thereof is 0.95, the specific surface area is 4,000 $m^2/m^3$ and the wire diameter is 1 mm. The volume of the rotating bed layers accounts for 45% of the total volume within the reactor housing. The stationary bed layers adopt the same wire fillers as the rotating bed layers and are 50% as thick as the rotating bed layers. Concentrated sulfuric acid of 95% by mass is used as the catalyst and isobutane and butene are used as raw materials to carry out the alkylation reaction.

The molar ratio of isobutane to butene is in a range from 1:1 to 300:1, preferably from 3:1 to 50:1. The volume ratio of acid to hydrocarbon is in a range from 0.1:1 to 5:1, preferably from 0.5:1 to 1.5:1. The reaction temperature ranges from −20 to 15° C., preferably from −10 to 10° C. and more preferably from −5 to 5° C. The reaction pressure ranges from 0.2 to 1.5 MPa, preferably from 0.3 to 0.8 MPa. The rotating bed rotates at a speed in a range from 50 to 5,000 rpm, preferably from 150 to 2,000 rpm. The residence time of the reactants in the reactor is generally in a range from 2 to 600 s, preferably from 10 to 100 s.

Nitrogen is used as the circulating cooling medium and the refrigeration system of the circulating cooling system adopts the ammonia refrigeration system.

The specific operation conditions are as shown in Table 1 and the reaction results as shown in Table 2.

Comparative Example 1

A conventional horizontal mechanical stirring reactor arranged with interior cooling tubes (see *Natural Gas and Oil*, Liu Zhigang, et al., 2002(2), "A review of isobutane and butene alkylation apparatuses", FIG. 2 for the structures) is adopted. The reaction conditions (the most optimized industrial operation conditions) and results are respectively listed in Table 1 and Table 2.

TABLE 1

Major alkylation conditions in the examples and comparative example

|  | Example 1 | Example 2 | Example 3 | Comparative example 1 |
|---|---|---|---|---|
| Ratio of isobutane to butene | 2:1 | 40:1 | 8:1 | 8:1 |
| Volume ratio of acid to hydrocarbon | 0.2:1 | 3:1 | 1:1 | 1:1 |
| Reaction temperature (° C.) | −5 | 0 | 6 | 6 |
| Reaction pressure (MPa) | 0.5 | 1.0 | 0.7 | 0.7 |
| Residence time (min) | 0.6 | 1 | 1.5 | 20 |
| Speed of the rotating bed (rmp) | 1,500 | 800 | 400 | — |

TABLE 2

Alkylation results in the examples and comparative example

|  | Example 1 | Example 2 | Example 3 | Comparative Example |
|---|---|---|---|---|
| Conversion of butene (mol %) | ~100 | ~100 | ~100 | ~100 |
| Acid consumption (kg of acid/t of alkylate oils) | 25 | 31 | 34 | 64 |
| Octane of alkylate oils (motor) | 92.6 | 92.1 | 91.3 | 90.5 |
| Reactor scale for the same processing amount (the volume calculated as a relative value) | 5 | 1.5 | 10 | 100 |

Examples 1 to 3 and Comparative Example 1 indicate that the alkylation reactor 100 according to the present disclosure is featured by low acid consumption, high product quality, etc.

Examples 4 to 6

The reactor 200 as indicated in FIG. 2 is adopted. The rotating bed layers comprise stainless steel mesh fillers and the bed voidage thereof is 0.95, the specific surface area is 4,000 $m^2/m^3$ and the wire diameter is 1 mm. The volume of the rotating bed layers accounts for 65% of the total volume within the reactor housing. Concentrated sulfuric acid of 95% by mass is used as the catalyst and isobutane and butene are used as raw materials to carry out the alkylation reaction.

The molar ratio of isobutane to butene is in a range from 1:1 to 300:1, preferably from 3:1 to 50:1. The volume ratio of acid to hydrocarbon is in a range from 0.1:1 to 5:1, preferably from 0.5:1 to 1.5:1. The reaction temperature ranges from −20 to 15° C., preferably from −10 to 10° C. and more preferably from −5 to 5° C. The reaction pressure ranges from 0.2 to 1.5 MPa, preferably from 0.3 to 0.8 MPa. The rotating bed rotates at a speed in a range from 50 to 5,000 rpm, preferably from 150 to 2,000 rpm. The residence time of the reactants in the reactor is generally in a range from 1 to 600 s, preferably from 10 to 100 s.

Nitrogen is used as the circulating cooling medium and the refrigeration system of the circulating cooling system adopts the ammonia refrigeration system.

Comparative Example 2 is the same as Comparative Example 1. The specific operation conditions are as shown in Table 3 and the reaction results as shown in Table 4.

TABLE 3

Major alkylation conditions in the examples and comparative example

|  | Example 4 | Example 5 | Example 6 | Comparative Example 2 |
|---|---|---|---|---|
| Molar ratio of isobutane to butene | 2:1 | 40:1 | 8:1 | 8:1 |
| Volume ratio of acid to hydrocarbon | 0.2:1 | 3:1 | 1:1 | 1:1 |
| Reaction temperature (° C.) | −5 | 0 | 6 | 6 |
| Reaction pressure (MPa) | 0.5 | 1.0 | 0.7 | 0.7 |
| Residence time (min) | 0.6 | 1 | 2 | 20 |
| Speed of the rotating bed (rpm) | 2,500 | 1,200 | 500 | — |

TABLE 4

Alkylation results in the examples and comparative example

|  | Example 4 | Example 5 | Example 6 | Comparative Example |
|---|---|---|---|---|
| Conversion rate of butene (mol %)) | ~100 | ~100 | ~100 | ~100 |
| Acid consumption (kg of acid/t of alkylate oils) | 21 | 26 | 32 | 64 |
| Octane of alkylate oils (motor) | 92.8 | 92.4 | 91.7 | 90.5 |
| Reactor scale for the same processing amount (the volume calculated as a relative value) | 5 | 1.5 | 10 | 100 |

It can be derived from Examples 4 to 6 and Comparative Example 2 that the alkylation reactor 200 according to the present disclosure is featured by low acid consumption, high product quality, etc.

The invention claimed is:

1. A reactor for reacting at least two liquid materials, comprising:
    an enclosed reactor housing;
    a feeding tube having at least two liquid material inlets, each inlet for receiving a corresponding liquid material;
    a distribution tube fluidly communicating with the feeding tube and extending into the reactor housing, the distribution tube having a plurality of distribution holes in a portion thereof extending into the reactor housing;

a rotating bed in form of a hollow cylinder, the rotating bed disposed in the reactor housing via a fixing mechanism so as to divide an inner cavity of the reactor housing into a central area and an outer area, the rotating bed being capable of rotating when driven by a driving mechanism; and an outlet provided in a lower portion of the reactor housing for outputting product after reaction, wherein the distribution tube extends into the central area spaced away from inner surface of the rotating bed so that the at least two liquid materials enter into the outer area from the central area through the rotating bed; and a stationary bed fixedly connected to the reactor, located in the outer area inside the reactor housing and spaced away from an outer side of the rotating bed.

2. The reactor according to claim 1, characterized in that the distribution holes on the distribution tube are all arranged under an upper surface of the rotating bed.

3. The reactor according to claim 1, characterized in that the upper surface of the rotating bed is fixedly provided with a first annular plate, which rotatably and sealably connects to a second annular plate fixedly mounted on an inner wall of the reactor housing.

4. The reactor according to claim 3, characterized in that a first flange is provided at a circumferential outer edge of the first annular plate, and a second flange is provided at a circumferential inner edge of the second annular plate, wherein the first and second flanges are sealably connected to each other in a relatively rotatable manner via a sealing member.

5. The reactor according to claim 1, characterized in that the rotating bed comprises a corrosion-resistant frame and a plurality of bed layers, each of the bed layers is composed of a corrosion-resistant wire mesh or filler.

6. The reactor according to claim 1, characterized in that the stationary bed extends around a circumference of the rotating bed in a range from 180 to 360 degrees.

7. The reactor according to claim 1, characterized in that an upper end of the stationary bed is fixedly arranged below the second annular plate.

8. The reactor according to claim 1, characterized in that the stationary bed is fixed on the inner wall of the reactor housing via a radial connecting member.

9. The reactor according to claim 1, characterized in that the stationary bed and the rotating bed are of the same height and have the same axis.

10. The reactor according to claim 7, characterized in that the stationary bed is longer than the rotating bed.

11. The reactor according to claim 1, characterized in that the stationary bed is 0.2 to 1.5 times as thick as the rotating bed in a radial direction.

12. The reactor according to claim 1, characterized in that an upper end of a chamber formed between the rotating bed and the stationary bed is closed by the second annular plate and a lower end thereof is open.

13. The reactor according to claim 1, characterized in that the reactor housing is further provided with a circulating cooling medium inlet and a circulating cooling medium outlet, wherein the inlet and the outlet are respectively arranged at two sides with respect to the upper surface of the rotating bed.

14. The reactor according to claim 13, characterized in that the circulating cooling medium inlet is provided above the upper surface of the rotating bed and the circulating cooling medium outlet is provided below a lower surface of the rotating bed.

15. The reactor according to claim 1, characterized in that at a top portion of the feeding tube a collision chamber is provided for premixing the at least two liquid materials, wherein the liquid material inlets communicate with and extend into the collision chamber.

16. The reactor according to claim 15, characterized in that an injection pipe is provided at each of the liquid material inlets, the injection pipes being opposite to each other.

17. The reactor according to claim 1, characterized in that the fixing mechanism comprises a rotating shaft connecting to the driving mechanism and a support connecting to the rotating shaft, wherein the rotating bed is mounted on the support.

18. The reactor according to claim 17, characterized in that the driving mechanism comprises an electric motor disposed outside the reactor housing.

19. The reactor according to claim 1, characterized in that the reactor is used for alkylation reaction.

20. The reactor according to claim 19, characterized in that each of the at least two liquid inlets respectively receives sulfuric acid and mixed hydrocarbons.

21. An alkylation reaction process, comprising:
feeding isobutene, a stream of mixed hydrocarbon of C3 to C5 olefins, and sulfuric acid into the reactor of claim 1, and
carrying out an alkylation reaction in the reactor of claim 1.

22. The process according to claim 21, wherein a molar ratio of isobutane to C3 to C5 olefins is in a range from 1:1 to 300:1.

23. The process according to claim 22, wherein in a volume ratio of the sulfuric acid to the mixed hydrocarbons is in a range from 0.1:1 to 5:1, and a mass concentration of the sulfuric acid is in a range from 90% to 97%.

24. The process according to claim 21, a temperature in the reactor housing is in a range from −20 to 15° C., and a pressure in the reactor housing is in a range from 0.2 to 1.5 MPa so that the mixed hydrocarbons are in a liquid phase.

25. The process according to claim 21, wherein the rotating bed rotates at a speed in a range from 50 to 5,000 rpm.

26. The process according to claim 21, wherein a residence time in the reactor is in a range from 2 to 600 s.

27. The process according to claim 21, a reaction temperature is controlled with the circulating cooling medium selected from the group consisting of nitrogen, hydrogen, inert gases, carbon monoxide, carbon dioxide, methane, ethane, propane, and mixtures thereof.

28. The process according to claim 27, wherein propane is introduced in the reactor as the circulating cooling medium in a liquid phase and discharged therefrom in a vapor phase.

* * * * *